(12) United States Patent
Burger et al.

(10) Patent No.: US 9,326,675 B2
(45) Date of Patent: May 3, 2016

(54) VIRTUAL VISION CORRECTION FOR VIDEO DISPLAY

(75) Inventors: Douglas Christopher Burger, Redmond, WA (US); David Alexander Molnar, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 693 days.

(21) Appl. No.: 12/647,076

(22) Filed: Dec. 24, 2009

(65) Prior Publication Data

US 2011/0157180 A1   Jun. 30, 2011

(51) Int. Cl.
*A61B 3/00* (2006.01)
*G06T 3/00* (2006.01)

(52) U.S. Cl.
CPC ............... *A61B 3/0041* (2013.01); *G06T 3/00* (2013.01)

(58) Field of Classification Search
None
See application file for complete search history.

(56) References Cited

U.S. PATENT DOCUMENTS

| | | | |
|---|---|---|---|
| 5,151,722 A | 9/1992 | Massof | |
| 5,201,034 A * | 4/1993 | Matsuura et al. | 715/865 |
| 5,451,976 A | 9/1995 | Ito | |
| 6,084,556 A * | 7/2000 | Zwern | 345/8 |
| 6,192,341 B1 * | 2/2001 | Becker et al. | 704/271 |
| 6,543,898 B1 * | 4/2003 | Griffin et al. | 351/243 |
| 6,592,223 B1 * | 7/2003 | Stern | A61B 3/028 351/239 |
| 6,784,905 B2 * | 8/2004 | Brown et al. | 715/865 |
| 7,062,547 B2 * | 6/2006 | Brown et al. | 709/221 |
| 2003/0030597 A1 | 2/2003 | Geist | |
| 2005/0153776 A1 | 7/2005 | LeMay | |
| 2005/0204295 A1 * | 9/2005 | Voorhees et al. | 715/747 |
| 2006/0238704 A1 * | 10/2006 | Donnerhacke et al. | 351/200 |
| 2008/0129957 A1 | 6/2008 | Mellon | |
| 2009/0089718 A1 * | 4/2009 | Pompilio et al. | 715/865 |
| 2009/0138268 A1 * | 5/2009 | Maehira et al. | 704/260 |
| 2009/0161225 A1 | 6/2009 | Liu | |
| 2010/0079356 A1 * | 4/2010 | Hoellwarth | 345/8 |
| 2011/0010646 A1 * | 1/2011 | Usey | 715/762 |

OTHER PUBLICATIONS

Carey, D., Virtual display glasses, up close and personal, EE Times India, Dec. 2007.
Spitzer, M. B., N. M. Rensing, R. W. McClelland, P. D. Aquilino, Eyeglass-based systems for wearable computing, First Int'l Symposium on Wearable Computers, Oct. 1997, pp. 48-51, Cambridge, Massachusetts, USA.

* cited by examiner

*Primary Examiner* — Daniel Hajnik
(74) *Attorney, Agent, or Firm* — Alin Corie; Cassandra T. Swain; Micky Minhas

(57) ABSTRACT

The virtual vision correction technique described herein pertains to a technique for determining a user's vision characteristics and/or adjusting a display to a user's vision characteristics. The virtual vision correction technique described herein provides vision correction for people with vision problems by making the video displayed adapt to the person's vision correction needs. In one embodiment of the technique, the user can state their vision prescription needs and the video displayed is processed to appear "20/20" to that person. Alternatively, the video display, for example, video display glasses, can "auto-tune" a representative image (such as an eye chart) to determine the appropriate video processing for that person.

20 Claims, 16 Drawing Sheets

VIRTUAL VISION CORRECTION FOR VIDEO DISPLAY

Video glasses, also known as video display glasses, are glasses that contain screens for display of various things such as pictures, movies, electronic mail and other applications. Video glasses have become more popular in recent years as they allow a user to view a movie, check their email, read text messages and participate in an augmented reality game in complete privacy. Video display glasses also have commercial and military applications. For example, video glasses can also be used to overlay information over real world scenes. They can be used to overlay maps over battle fields or fire zones.

Using video glasses is difficult for people who need vision correction. The displays in video glasses are typically mounted into the glasses assuming the viewer has 20/20 vision. This leads to poor image quality for people that do not have perfect vision. People with imperfect vision may wear contacts (which may not be feasible for all corrections) or custom fit lenses over or under the video glasses. Alternately, existing video glasses may require users to fit them with special corrective lenses tailored to their prescription.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The virtual vision correction technique described herein can provide for the discovery of a user's vision correction needs and can provide vision correction for people with vision problems by making video displayed adapt to a person's vision correction needs. The vision discovery and display adaptation features of the technique can each be employed separately, or can both be employed in concert.

The virtual vision correction technique, in one embodiment, allows a user to state their vision prescription needs. Input video is then processed to appear "20/20" to that person when the processed video is displayed. Alternatively, the technique can employ a representative image (such as an eye chart, for example) to determine a user's vision characteristics. Video processing can then be performed once a user's vision characteristics are obtained to adapt input video to be displayed in accordance with a user's vision correction needs.

The virtual vision correction technique pre-processes an image or video input for display based on the user's vision correction needs by transforming the input image or video. Instead of using additional after-market lenses placed in front of the video glasses, the technique can just change the video displayed. Furthermore, the technique in an "auto-tune" mode can accommodate changes in vision over time, without the need for additional hardware or additional lens purchases, by prompting a user to provide feedback as to the processed video displayed, using user input to further enhance or correct the image/video displayed to the user.

DESCRIPTION OF THE DRAWINGS

The specific features, aspects, and advantages of the disclosure will become better understood with regard to the following description, appended claims, and accompanying drawings where:

FIG. 16 is a schematic of an exemplary computing device which can be used to practice the virtual vision correction technique.

DETAILED DESCRIPTION

In the following description of the virtual vision correction technique, reference is made to the accompanying drawings, which form a part thereof, and which show by way of illustration examples by which the virtual vision correction technique described herein may be practiced. It is to be understood that other embodiments may be utilized and structural changes may be made without departing from the scope of the claimed subject matter.

1.0 Virtual Vision Correction Technique.

The following sections provide an overview of the virtual vision correction technique, as well as exemplary systems and processes for employing the technique.

1.1 Overview of the Technique

Figure 1:
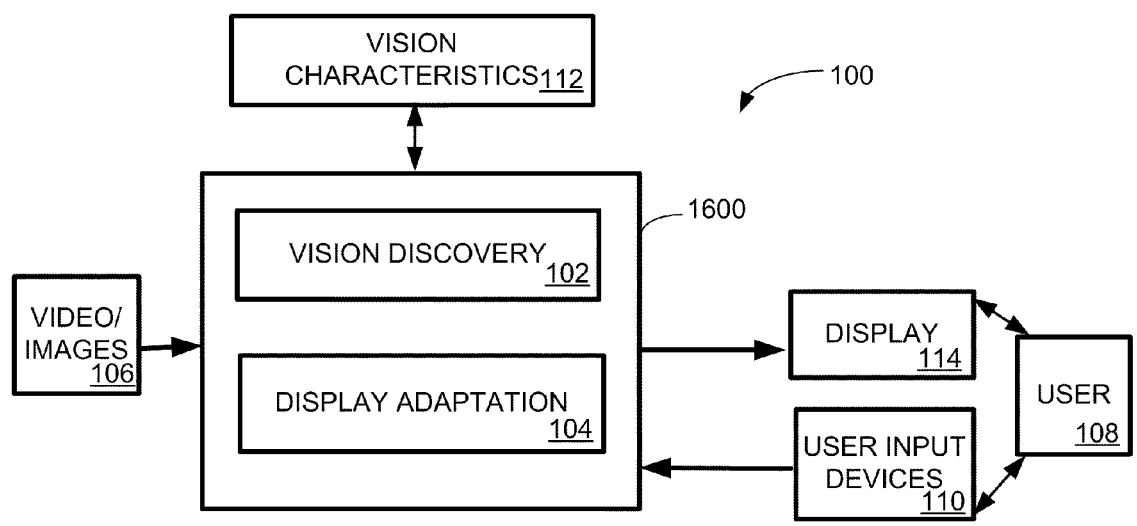
FIG. 1 depicts a high level overview of an exemplary embodiment of the virtual vision correction technique described herein.

FIG. 1 provides a high level diagram of one exemplary embodiment of an architecture 100 for employing the virtual vision correction technique. As shown in FIG. 1, the virtual vision correction technique may employ two major components, a vision discovery component (block 102) and a display adaption component (block 104), of which either or both components can be used separately or together. The vision discovery component (block 102) and the display adaption component (block 104) reside on a computing device (block 1600) which will be described in greater detail with respect to FIG. 16. Video or one or more images (block 106) are input into the computing device 1600, and are processed by the vision discovery component (block 102) and/or the display adaption component (block 104). The processed images and video can be output to a display (block 114). For example, this display (block 114) could be a pair of video display glasses, a laptop display, a display on the wall, or any other display device. The vision characteristics (block 112) of the user (block 108) can be determined by the vision discovery module 102 and used to adapt the display (block 114) to these vision characteristics. Alternately, a user's vision display characteristics can be explicitly provided/input in order to adapt the input image/video to the display. The technique can also obtain user feedback via input devices (block 110) from a user (block 108) to discover the user's changing vision characteristics and adapt the images/video displayed to these characteristics based on the user feedback.

In general, the vision discovery component (block 102) determines the user's vision characteristics. The display adaption component (block 104) changes the video displayed to accommodate the user's vision characteristics. The display adaption component 104 can also "auto-tune" (e.g., adjust) the display based on user feedback. In this case, the auto-tune logic is responsible for detecting user dissatisfaction with the display and prompting the user for feedback to adjust the display.

Figure 2:
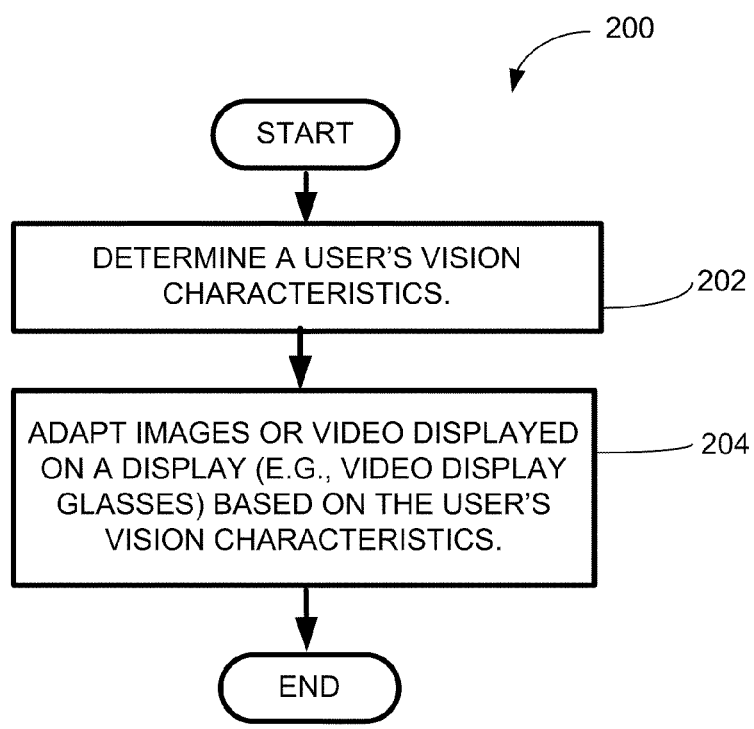
FIG. 2 depicts a high level flow diagram of an exemplary process for employing the virtual vision correction technique described herein.

A high level flow diagram for a process for employing one embodiment of the virtual vision correction technique is shown in FIG. 2. As shown in block 202, a user's vision characteristics are determined or obtained. The user's vision characteristics are used to adapt input images or video to be displayed based on the user's vision characteristics, as shown in block 204.

Contrasted with the existing solution of using corrective lenses fitted to video glasses after manufacture, the virtual vision correction technique described herein requires no additional parts and no additional expense over and above conventional video glasses when used to display images/video on them. Contrasted with the use of regular glasses for correcting vision, the technique does not require wearing two pairs of glasses at once, which is unsightly at best and impossible at worst. Contrasted with the use of contacts, the technique works for people who cannot or choose not to wear contact lenses.

It should be noted that while the description provided herein focuses on the use of the virtual vision correction technique with video display glasses, the technique can be employed with any type of display.

1.2 Exemplary Vision Discovery System.

Figure 3:
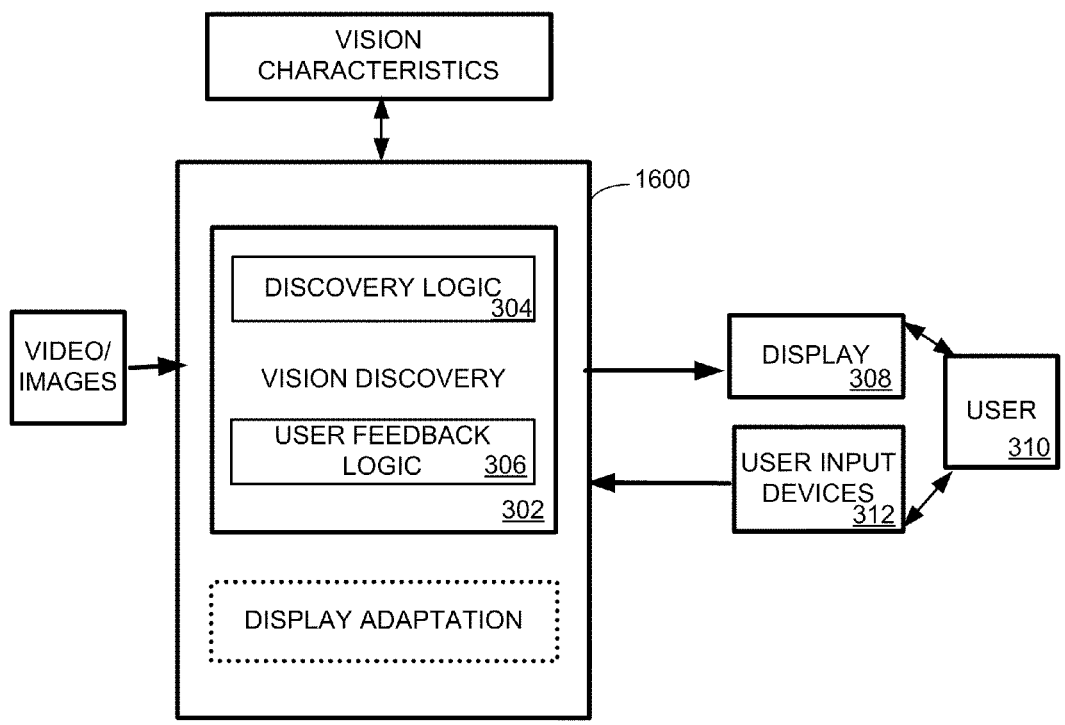
FIG. 3 depicts a high level overview of an exemplary embodiment of a vision discovery module of the virtual vision correction technique described herein.

FIG. 3 provides an exemplary diagram of a vision discovery system/component for employing one embodiment of the virtual vision correction technique. A vision discovery module 302 resides on a computing device 1600, mentioned previously and to be discussed in greater detail with respect to FIG. 16. The vision discovery module (block 302) includes a vision discovery logic module (block 304) and a user feedback logic module (block 306) which ultimately interface with the display (block 308) (e.g., video display glasses) and user input devices (block 312) which receive input and provide data to a user (block 310). The following paragraphs describe these components.

The computing device 1600 can be any computational device, such as, for example, a mobile phone (e.g., running an operating system for mobile devices), a net book computer, a lap top computer, a desk top computer, a Personal Data Assistant (PDA), and so forth.

In one embodiment of the technique, the display (block 308) can be any type of display. Such a display may be a conventional LCD monitor, a wall display or video glasses with integrated display unit. In the case of video glasses, these glasses may be opaque, may employ see-through overlays, may use LEDs, and may use lasers and other display technology. The discovery logic module (block 304) is responsible for creating a display to test a user's vision. The user feedback logic (block 306) is responsible for processing user input. The user input device (block 312) can be one of many devices for processing user input, such as, for example, a keypad, a microphone, a touch screen, a button, an accelerometer, or other any other input device.

The vision discovery module (block 302) can use a variety of methods to discover the user's vision characteristics. These can include displaying an eye chart on the display and asking a user to type in the letters they see on each line of the eye chart, using a keypad to provide this input. This eye chart can be a typical Snellen eye chart or could be any other image usable to test for a user's vision characteristics. Alternately, for example, the vision discovery module (block 302) can employ an eye chart and a touch screen. In this case, the vision discovery module can ask the user to touch the line of the eye chart that the user cannot read clearly in order to determine the user's vision characteristics. Another alternative for determining a user's vision characteristics is using an eye chart and a microphone. In this case, the user can merely state the first line of the eye chart that they can not read clearly. Still another alternative to determine the user's vision characteristics is to apply a color blindness (Ishihara) test, by asking the user to input the symbol or numeral they see in an Ishihara test and comparing this to what would be expected for someone who is not color blind.

The following paragraphs provide additional details on some of the vision discovery processes employed by the virtual vision correction technique described herein.

1.2.1 Exemplary Processes Employed by the Vision Discovery Module of the Virtual Vision Correction Technique.

Figure 4:
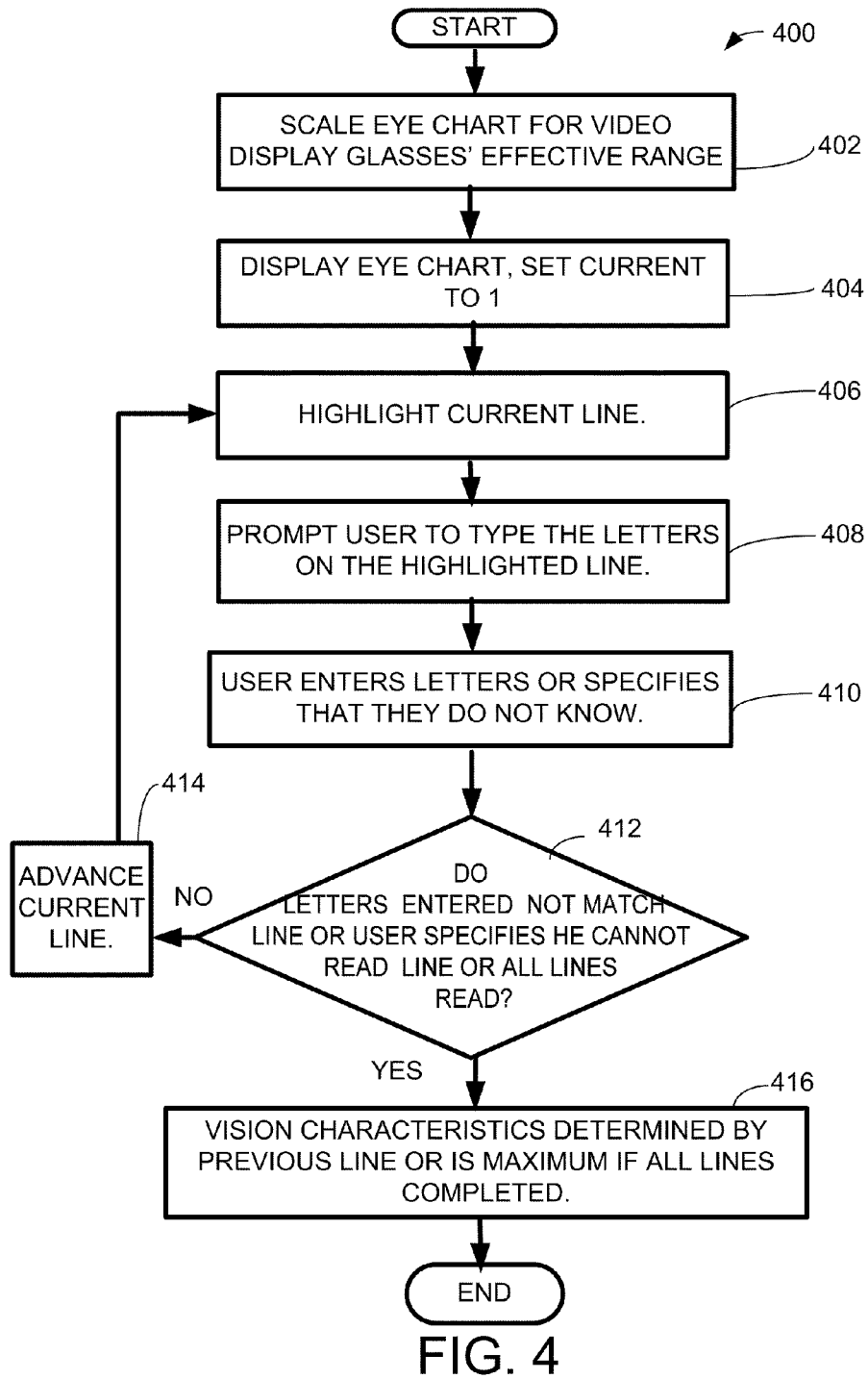
FIG. 4 is a flow diagram depicting an exemplary embodiment of a process for employing the virtual vision correction technique described herein wherein an eye chart and a key pad are used in discovering a user's vision correction needs.

FIG. 4 provides a flow diagram of one exemplary process 400 employed by the virtual vision correction technique in order to discover a user's vision characteristics by using a display and keypad. As shown in FIG. 4, block 402, an eye chart is scaled for a display's (e.g., the video display glasses') effective range. For example, video display glasses are typically built to simulate the experience of looking at a TV screen from a certain number of feet away. For wall-mounted or other displays, the person viewing the chart may be closer or farther away from the display. This is an issue because a typical eye chart, for example, the Snellen eye chart is calibrated assuming that each line in the chart is a certain apparent size for the person taking the eye test. Therefore, the virtual vision correction technique makes the eye chart (e.g., Snellen chart) larger or smaller depending on the specific characteristics of the display. Otherwise the results of the test, i.e. which lines the user can or cannot read, will not appropriately reflect the user's vision characteristics. Once the eye chart is scaled for a display's effective range, the eye chart is displayed to the user, setting the current line to 1, as shown in block 404. The current line is highlighted (block 406) and a prompt appears to the user to type the letters on the highlighted line (block 408). The user either enters the letters with a keypad or specifies that they cannot read the letters of the current line (block 410). If the user enters the letters he or she sees on the current line, the technique determines if the letters the user entered match the current line on the eye chart (block 412). If yes, the current line is advanced (block 414) and blocks 406, 408, 410 and 412 are repeated for all subsequent lines until the user's input does not match the current line in the eye chart, the user specifies that they cannot read the line, or until the user reads all lines. If the letters typed by the user do not match the eye chart, or the user specifies that they cannot read the current line, the user's vision characteristics are determined by the previous line (block 416). If the user can read all lines of the eye chart then the user's vision is of maximum quality and no correction is needed (block 416).

Figure 5:
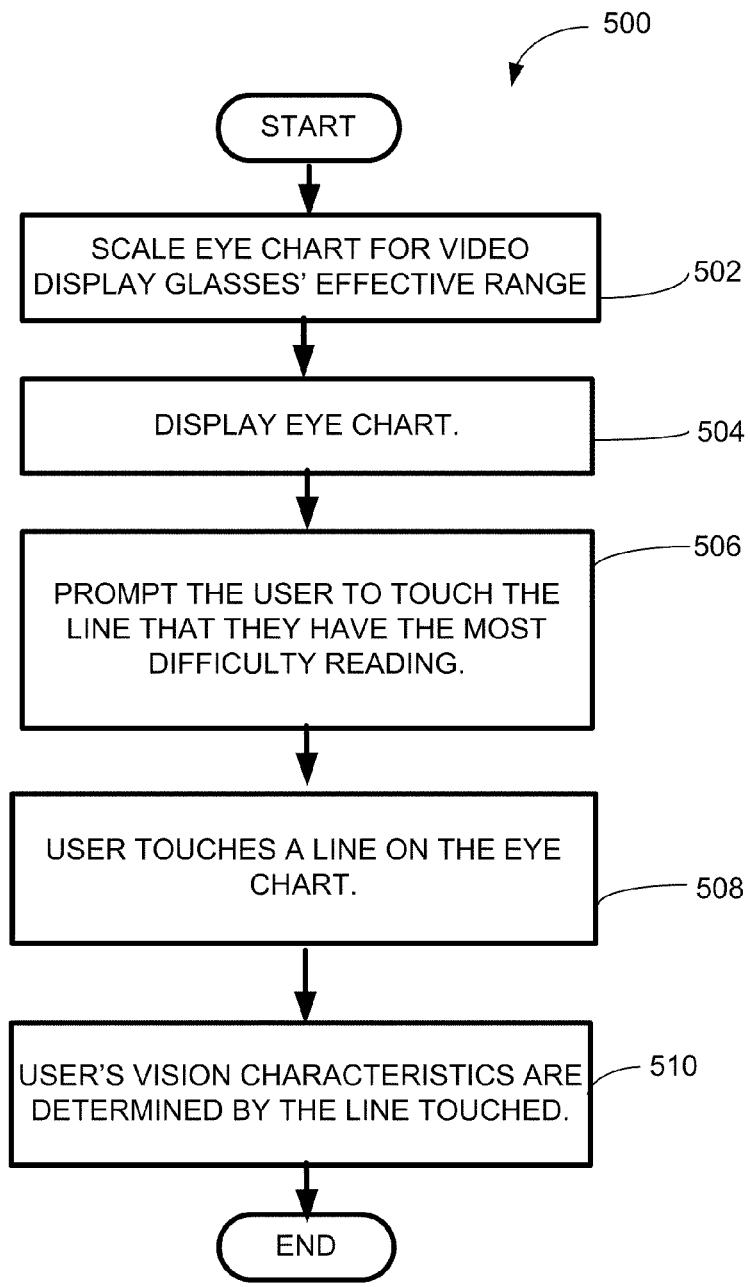
FIG. 5 is a flow diagram depicting an exemplary embodiment of a process for employing the virtual vision correction technique described herein wherein an eye chart and a touch screen are used in discovering a user's vision correction needs.

FIG. 5 provides a flow diagram of another exemplary process 500 which can be employed by the virtual vision correction technique in order to discover a user's vision characteristics by using a display with a touch screen. As shown in FIG. 5, block 502, an eye chart is scaled for the display's (e.g., the video display glasses') effective range. The eye chart is displayed to the user (block 504). The user is prompted to touch the line that they are having the most difficulty reading (block 506). The user touches the line that they are having the most difficulty reading on the eye chart (block 508) and the user's vision characteristics are determined by the line touched (block 510).

Figure 6:
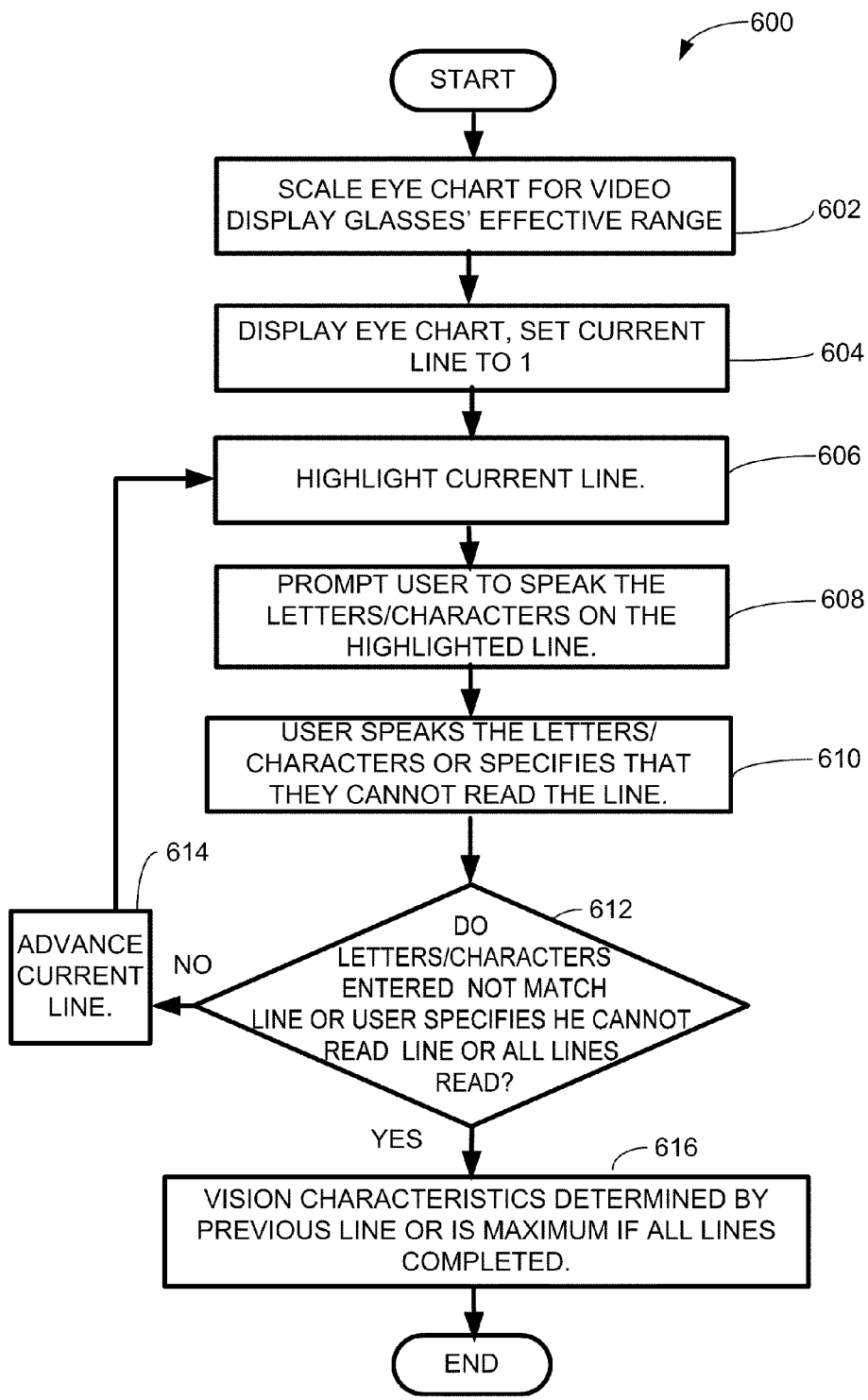
FIG. 6 is a flow diagram depicting an exemplary embodiment of a process for employing the virtual vision correction technique described herein wherein an eye chart and microphone are used in discovering a user's vision correction needs.

FIG. 6 provides a flow diagram of yet another exemplary process 600 which can be employed by the virtual vision correction technique in order to discover a user's vision characteristics by using a display and a microphone. As shown in FIG. 6, block 602, an eye chart is scaled for the display's (e.g., the video display glasses') effective range. The eye chart is displayed to the user, setting the current line to 1, as shown in block 604. The current line is highlighted (block 606) and the user is prompted to speak the letters on the highlighted line (block 608). The user either speaks the letters on the current line into the microphone or specifies that they cannot read the highlighted line (block 610). The technique determines if the letters match the eye chart (block 612). If yes, the current line is advanced (block 614) and blocks 606, 608, 610 and 612 are repeated for all subsequent lines until the user's input does not match the current line in the eye chart, the user specifies that they cannot read the current line (blocks 610, 614) or the user reads all lines. If the letters spoken by the user do not match the eye chart, or they cannot read the current line, the user's vision characteristics are determined by the previous line (block 616). Otherwise the user does not need vision correction.

Figure 7:
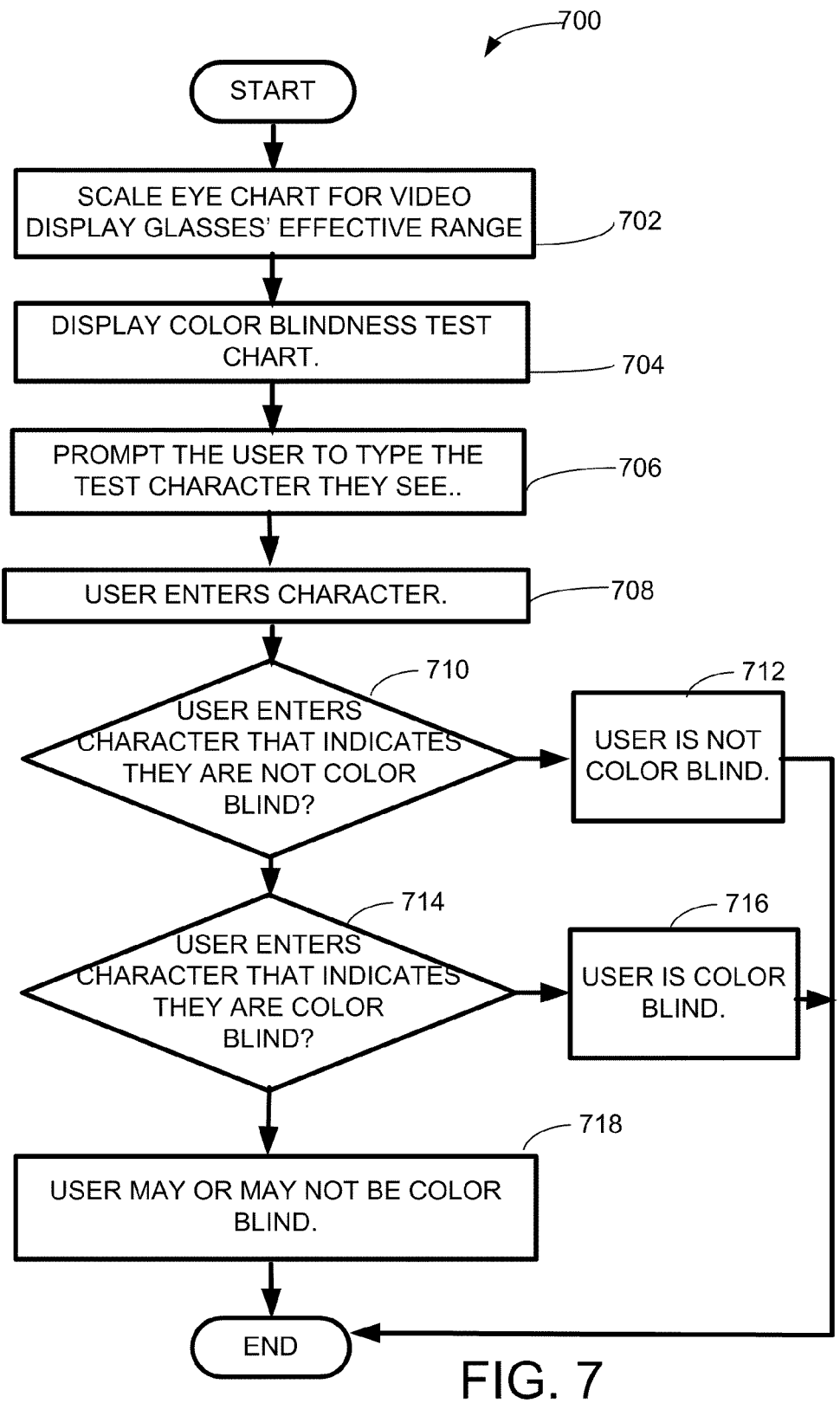
FIG. 7 is a flow diagram depicting an exemplary embodiment of a process for employing the virtual vision correction technique described herein wherein a color blindness test chart is used in discovering a user's vision correction needs.

FIG. 7 provides a flow diagram of yet another exemplary process 700 that can be employed by the virtual vision correction technique in order to discover a user's vision characteristics by using a display and an input device such as a keypad. As shown in FIG. 7, block 702, a color blindness test chart is scaled for the display's (e.g., the video display glasses') effective range. The color blindness test chart is displayed to the user (block 704) and the user is prompted to type in or speak the number/character they see in the color blindness test chart if the use is not color blind (block 706). The user responds (block 708) and the technique determines if the user's response matches the expected number/character displayed on the color blindness test chart (block 710). If yes, the user in determined not to be color blind (block 712). If the user responds with the wrong number/character, indicating color blindness, the user is determined to be definitely color blind (block 714, 716). If the user responds with a different number/character the user is determined to be possibly color blind (block 718).

1.3 Exemplary Display Adaptation System.

Figure 8:
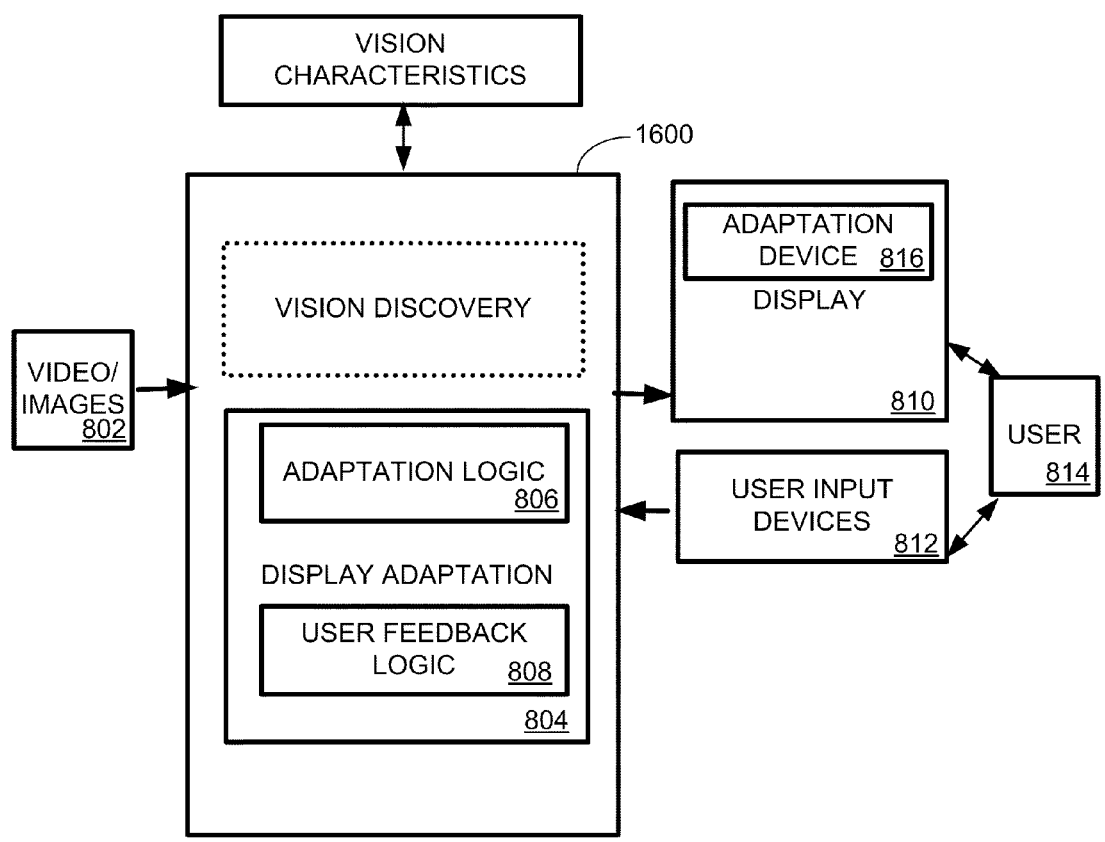
FIG. 8 depicts a high level overview of an exemplary embodiment of a display adaptation module of the virtual vision correction technique described herein.

FIG. 8 provides an exemplary diagram of a display adaptation system or component 800 employed in one embodiment of the virtual vision correction technique. A display adaptation module 804 resides on a computing device 1600, mentioned previously and to be discussed in greater detail with respect to FIG. 16. The display adaptation module 804 includes an adaptation logic module 806 and a user feedback logic module 808 which interface with the display 810 (e.g., video display glasses) and one or more user input devices (block 812) which receive input and provide data to a user (block 814). These components are described in the following paragraphs.

As discussed previously, the computing device 1600 can be any computational device, such as, for example, a mobile phone running an operating system for mobile devices, a net book computer, a lap top computer, a desk top computer, a PDA, and so forth.

The display (block 810) can be any type of display, as discussed previously. For example, in the case of video display glasses, they may be opaque, may employ see-through overlays and may use LEDs, lasers and other display technology. The adaptation logic module (block 806) is responsible for modifying the video displayed to accommodate a user's vision characteristics. The user feedback logic (block 808) is responsible for processing user input. The user input device or devices (block 812) can be one of many devices for processing user input, such as, for example, a keypad, a microphone, a touch screen, a button, an accelerometer, or other input. The display (block 810) can also include additional adaptation devices (block 816), such as, for example, hardware additions to video display devices to aid display adaptation, e.g. a graphics processor, special lenses, or others adaptation devices.

The display adaptation module (block 804) can use a variety of methods to adapt the video displayed to the user's vision characteristics. These can include focus change, edge emphasis, font size change and color palette change, among others. The display adaption component (block 804) can also "auto-tune" (e.g., adjust) the display based on user feedback. The auto-tune aspect of the virtual vision correction technique will be discussed in greater detail later.

1.3.1 Exemplary Processes Employed by the Display Adaption Module of the Virtual Vision Correction Technique.

Figure 9:
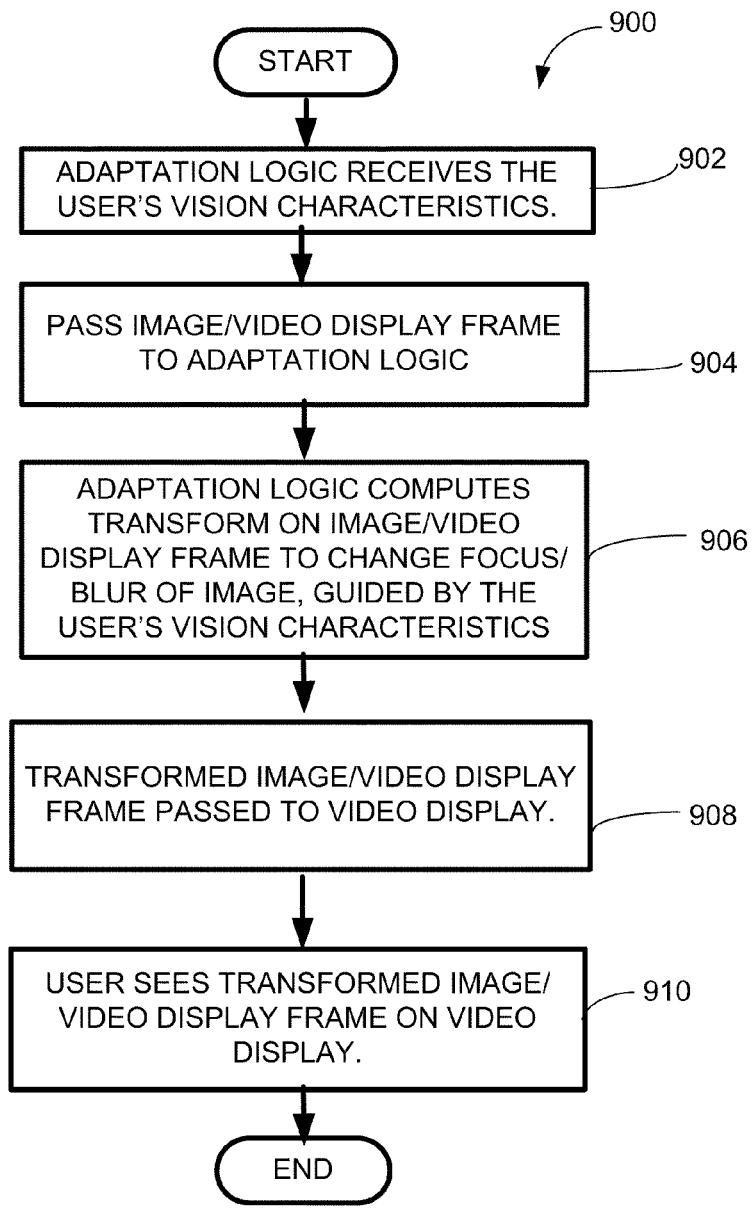
FIG. 9 is a flow diagram depicting an exemplary embodiment of a process for employing the virtual vision correction technique described herein wherein focus change is used to adapt a display to a user's vision correction needs.

FIG. 9 provides a flow diagram of one exemplary process 900 employed by the virtual vision correction technique in order to adapt a display to a user's vision characteristics. As shown in FIG. 9, blocks 902 and 904, the adaptation logic of the virtual vision correction technique receives the user's vision characteristics. This can occur, for example, by explicitly receiving these vision characteristics or determining the user's vision characteristics via the vision discovery processes previously discussed. In one embodiment of the virtual vision correction technique, the adaptation logic computes a transform on the images or video display frames input to change the focus/blur of these frames, as shown in blocks 904 and 906. The transformed images or video display frames are then passed to the display (e.g., the video display glasses), as shown in block 908. The user sees the transformed images or video on the display, as shown in block 910.

Figure 10:
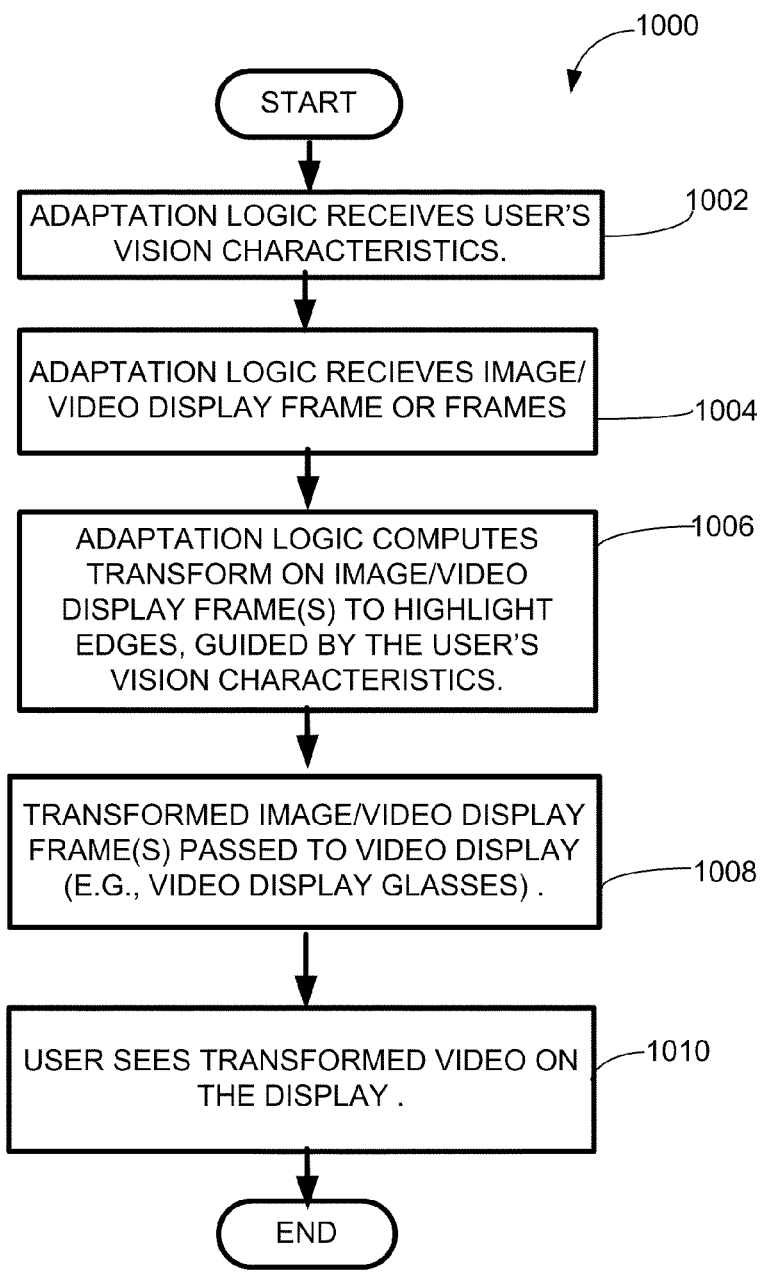
FIG. 10 is a flow diagram depicting an exemplary embodiment of a process for employing the virtual vision correction technique described herein wherein edge emphasis is used to adapt a display to a user's vision correction needs.

FIG. 10 provides another flow diagram of another exemplary process 1000 employed by the virtual vision correction technique in order to adapt a display to a user's vision characteristics. As shown in FIG. 9, blocks 1002 and 1004, the adaptation logic receives the user's vision characteristics and one or more images or video display frames. The adaptation logic computes a transform on the images/video display frames input to highlight edges, guided by the user's vision characteristics, as shown in block 1006. The transformed images/video display frames are then passed to the display (e.g., the video display glasses), as shown in block 1008. The user sees the transformed images or video display frames on the display (block 1010).

Figure 11:
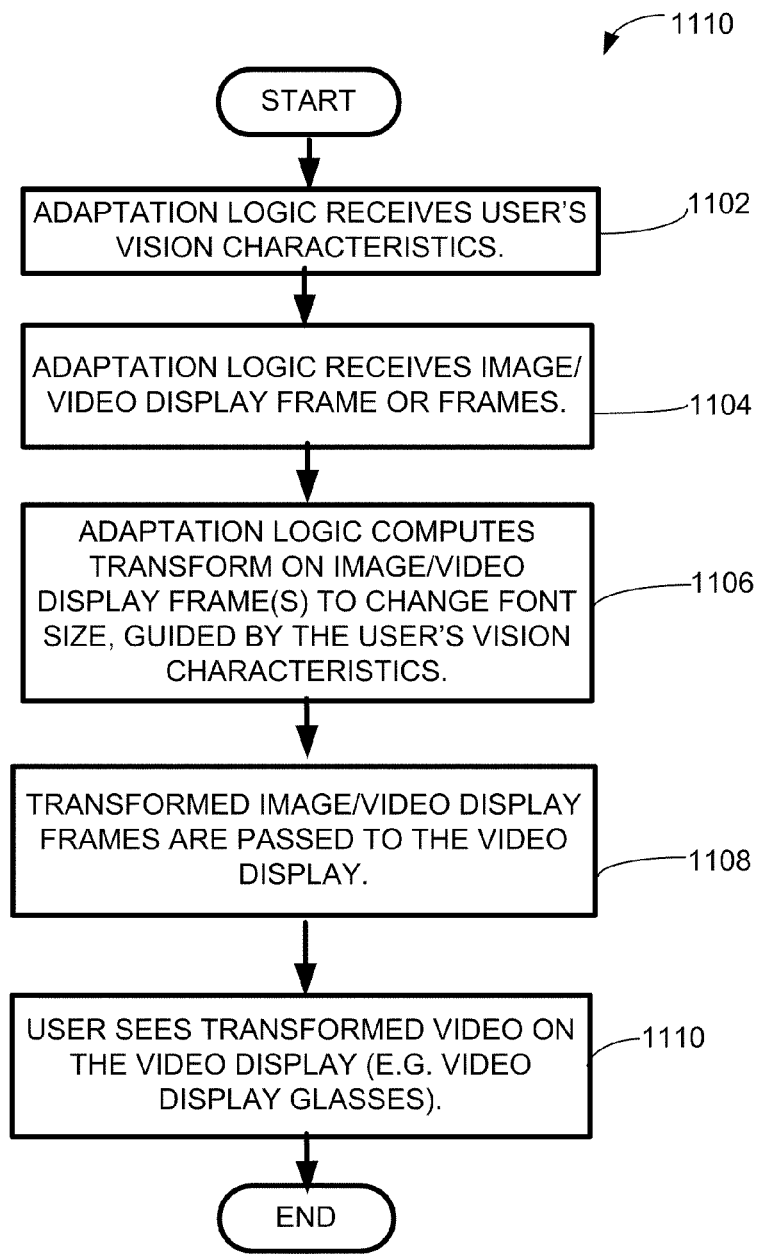
FIG. 11 is a flow diagram depicting an exemplary embodiment of a process for employing the virtual vision correction technique described herein wherein font magnification is used to adapt a display to a user's vision correction needs.

FIG. 11 provides yet another flow diagram of yet another exemplary process 1100 employed by the virtual vision correction technique in order to adapt a display to a user's vision characteristics. In this embodiment the font displayed is magnified. As shown in FIG. 11, blocks 1102 and 1104, the adaptation logic receives the user's vision characteristics and images/video display frames. The adaptation logic computes a transform on the images/video display frames to change the font size, as shown in block 1106. The transformed images/video display frames are then passed to the display (e.g., the video display glasses), as shown in block 1108. The user sees the transformed images/video display frames on the display (block 1110).

Figure 12:
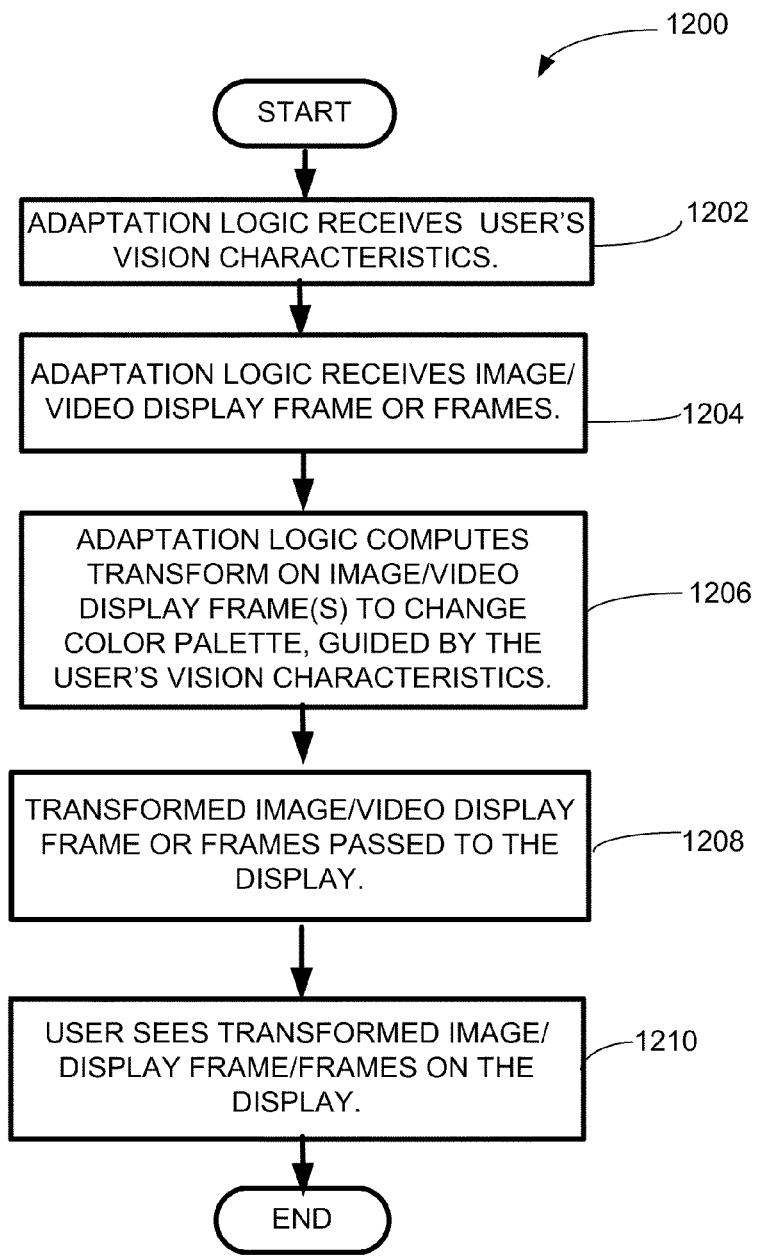
FIG. 12 is a flow diagram depicting an exemplary embodiment of a process for employing the virtual vision correction technique described herein wherein a color palette change is used to adapt a display to a user's vision correction needs.

FIG. 12 provides another flow diagram of another exemplary process 1200 employed by the virtual vision correction technique in order to adapt a display to a user's vision characteristics. In this embodiment the color palette displayed to a user is changed based on the user's vision characteristics. As shown in FIG. 12, blocks 1202 and 1204, the adaptation logic receives the user's vision characteristics and input images or video display frames. The adaptation logic computes a transform on the images or video display frame/frames input to change the color palette of the images or video display frames, as shown in block 1216. The transformed images or video display frames are then passed to the display (e.g., the video display glasses), as shown in block 1208. The user sees the transformed frame or frames on the display (block 1210).

1.4 Exemplary Display Adaptation System with Auto-Tune.

Figure 13:
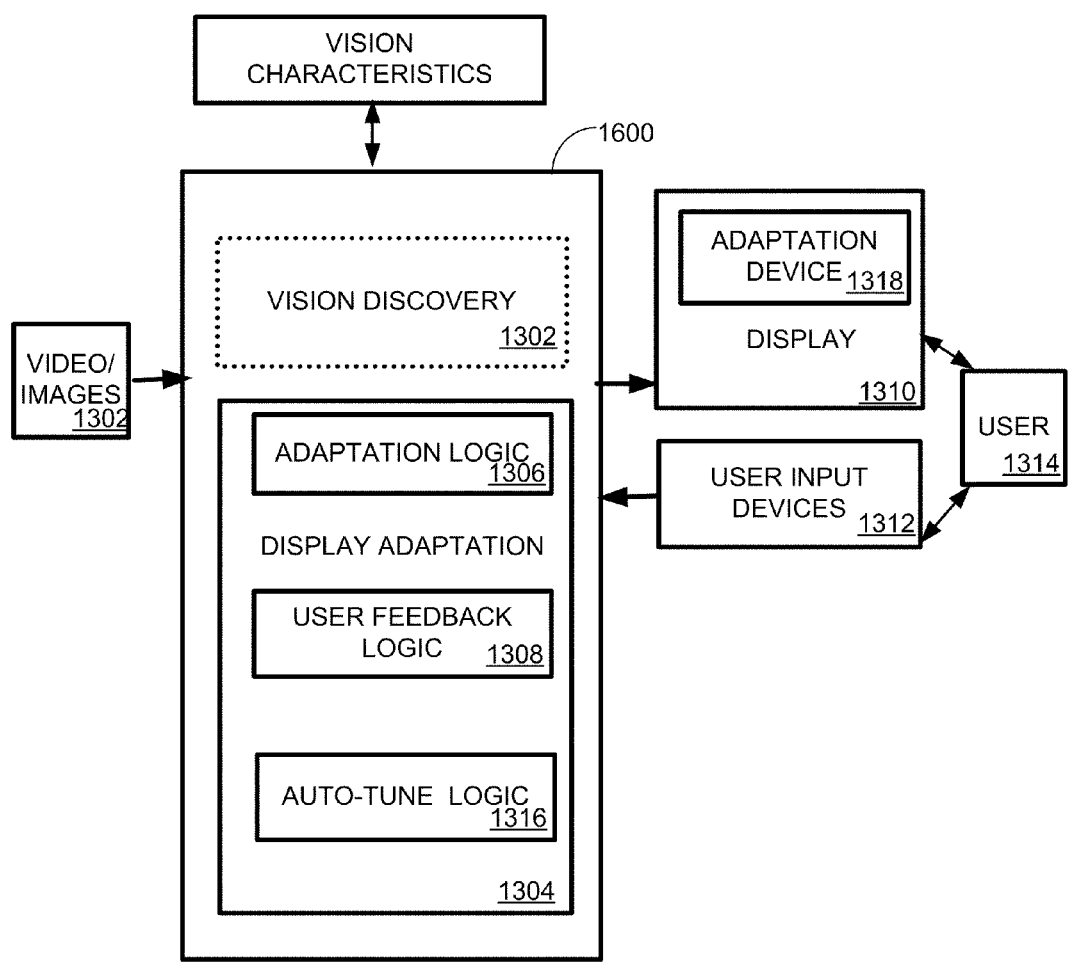
FIG. 13 depicts a high level overview of an exemplary embodiment of a display adaptation module that includes auto-tune logic of the virtual vision correction technique described herein.

FIG. 13 provides an exemplary diagram of a display adaptation component of one embodiment of the virtual vision correction technique that includes an auto-tune logic module (block 1306). This display adaptation module (block 1304) resides on a computing device 1600, mentioned previously and to be discussed in greater detail with respect to FIG. 16. The display adaptation module (block 1304) includes an adaptation logic module (block 1306) and a user feedback logic module (block 1308) which interface with the display (block 1310) and user input devices (block 1312) which receive input and provide data to a user (block 1314). This embodiment of the display adaptation component (block 1304) also includes an auto-tune logic module (block 1316) that determines user dissatisfaction with the display (block 1310) and prompts the user in order to adjust the display in accordance with the user's desires. These components are described in the following paragraphs.

As discussed with respect to previous embodiment of the virtual vision correction technique, the computing device 1600 can be any computational device, such as, for example, a mobile phone, a net book computer, a lap top computer, a desk top computer, a PDA, and so forth.

The display (block 1310) can be any type of display, such as a laptop computer display, a computer monitor, a wall display or video display glasses, for example. For example, in the case of video display glasses, they may be opaque, may employ see-through overlays, may use LEDs, and may use lasers or other display technology. The adaptation logic module (block 1306) is responsible for modifying the video displayed on the display (block 1310) to accommodate a user's vision characteristics. The user feedback logic (block 1308) is responsible for processing user input. The user input device or devices (block 1312) can be one of many devices for processing user input, such as, for example, a keypad, a microphone, a touch screen, a button, an accelerometer or other input device. The display (block 1310) can also include additional adaptation devices (block 1318), such as, for example, hardware additions to video display devices to aid display adaptation, e.g. a graphics processor, special lenses.

The display adaption component (block 1304) can also "auto-tune" (e.g., adjust) the display based on user feedback. In this case, the auto-tune logic module (block 1316) is responsible for detecting user dissatisfaction with the display (block 1310) and prompting the user for feedback to adjust the display.

1.4.1 Exemplary Processes Employed by the Vision Adaptation Module with Auto-Tune of the Virtual Vision Correction Technique.

The display adaptation module with auto-tune can auto-tune the display in a number of ways. For example, the vision adaptation module with auto-tune can detect and reduce typographical error frequency (e.g., based on the number of user keystrokes), or scale the font on a display until the user says to stop.

Figure 14:
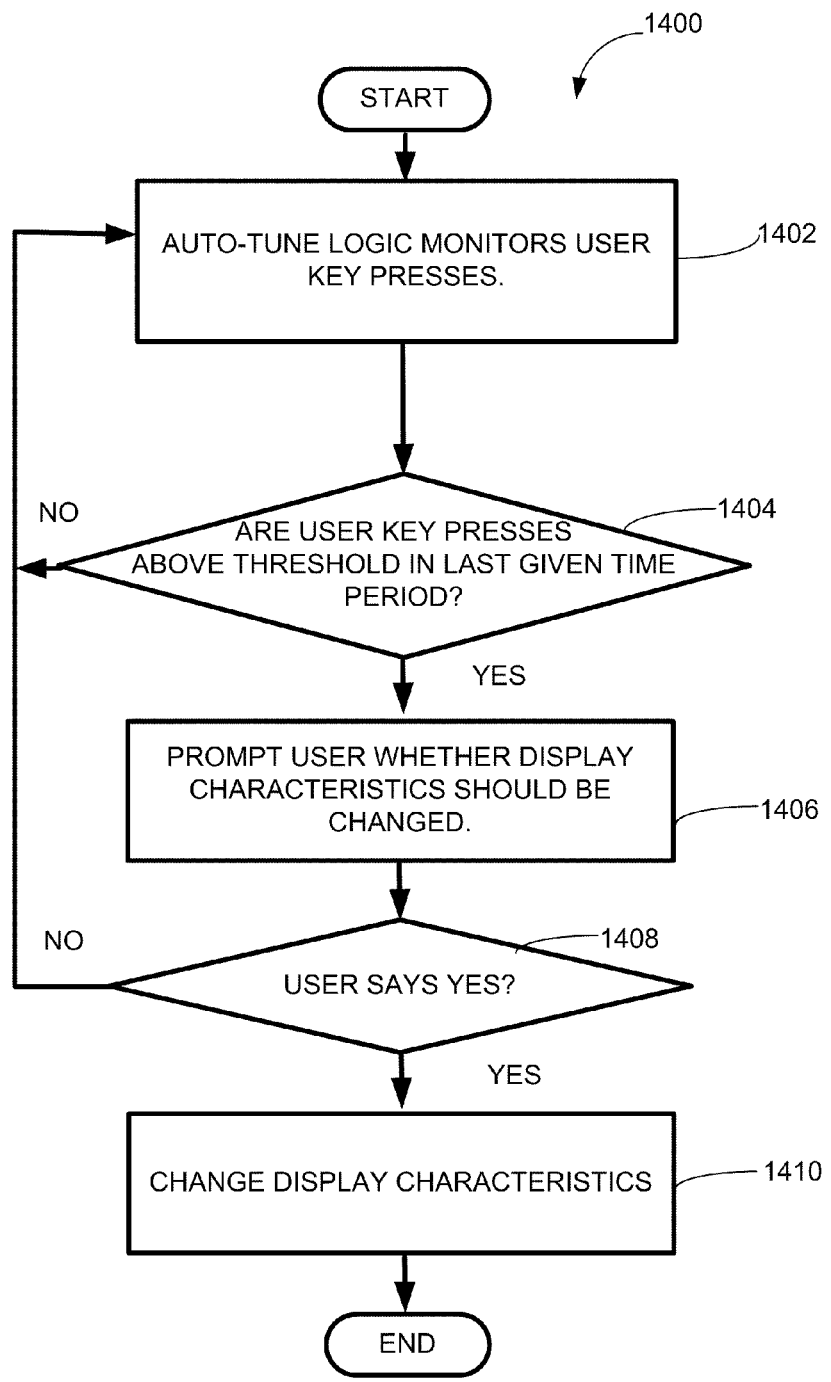
FIG. 14 is a flow diagram depicting an exemplary embodiment of a process for employing the virtual vision correction technique described herein wherein auto-tune logic is used to adapt a display to a user's vision correction needs by attempting to correct for typographical errors.

FIG. 14 provides a flow diagram of one exemplary process 1400 employed by the virtual vision correction technique in order to adapt a display to a user's vision characteristics using auto-tune logic. As shown in block 1402, the auto-tune logic module monitors key presses. The auto-tune logic determines if the user key presses are above a threshold determined in a previous time period. If so, the auto-tune logic asks the user if they would like to change the display characteristics (block 1404), and if the user so desires, the display characteristics are changed (blocks 1406, 1408, 1410).

Figure 15:
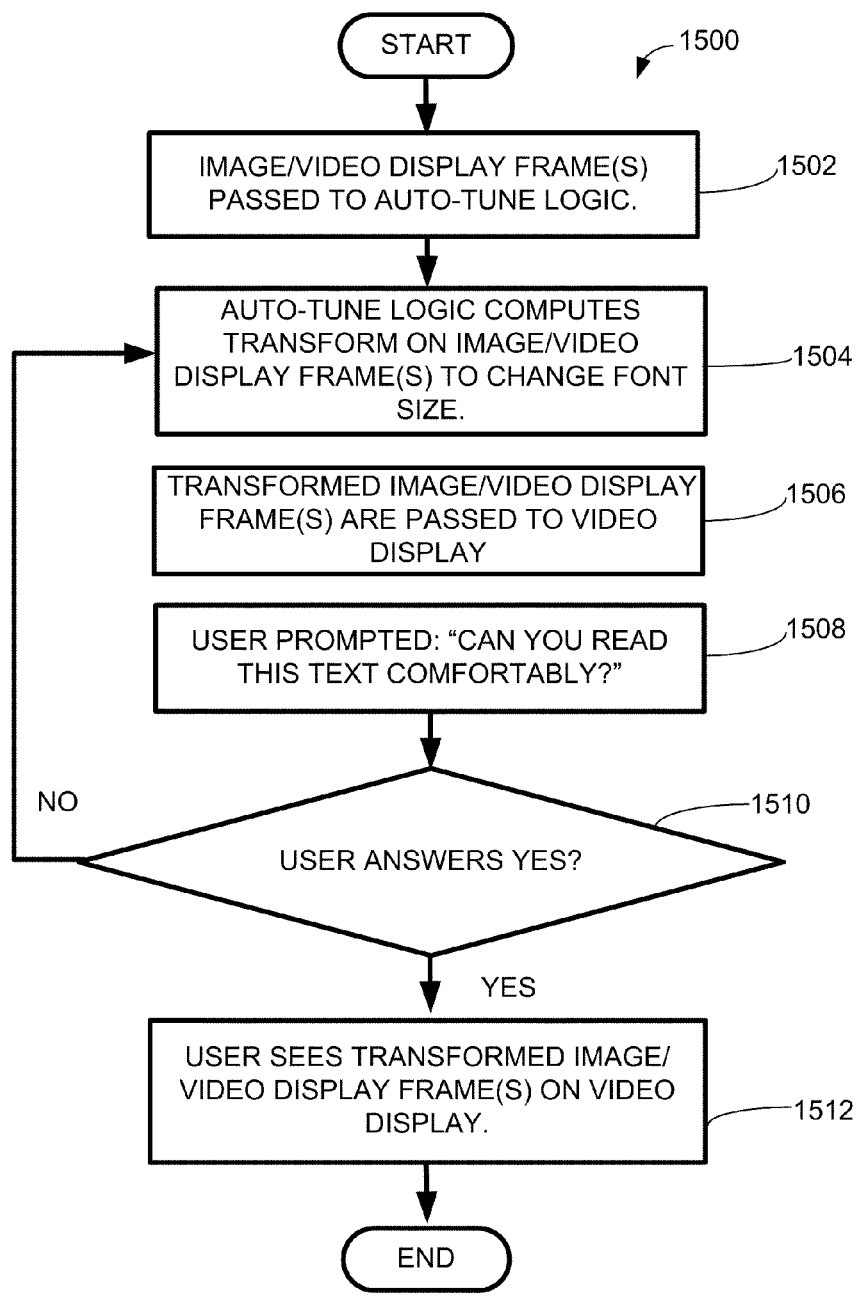

FIG. 15 provides another flow diagram of another exemplary process 1500 employed by the virtual vision correction technique in order to adapt a display to a user's vision characteristics using auto-tune logic. As shown in FIG. 14, block 1502, the adaptation logic of the technique passes a video display frames to the auto-tune logic. The auto-tune logic computes a transform on the video display frame to change the font size of the input video display frames, as shown in block 1504. The transformed video display frame or frames are then passed to the display (e.g., the video display glasses), as shown in block 1506. The user is prompted as to whether then can read the text comfortably (block 1508). If the user cannot read the text comfortably, blocks 1504, 1506 and 1508 are repeated. Once the user can read the text comfortably the user sees the transformed display on the display (block 1510 and 1512).

2.0 The Computing Environment

The virtual vision correction technique is designed to operate in a computing environment. The following description is intended to provide a brief, general description of a suitable computing environment in which the virtual vision correction technique can be implemented. The technique is operational with numerous general purpose or special purpose computing system environments or configurations. Examples of well known computing systems, environments, and/or configurations that may be suitable include, but are not limited to, personal computers, server computers, hand-held or laptop devices (for example, media players, notebook computers, cellular phones, personal data assistants, voice recorders), multiprocessor systems, microprocessor-based systems, set top boxes, programmable consumer electronics, network PCs, minicomputers, mainframe computers, distributed computing environments that include any of the above systems or devices, and the like.

Figure 16:
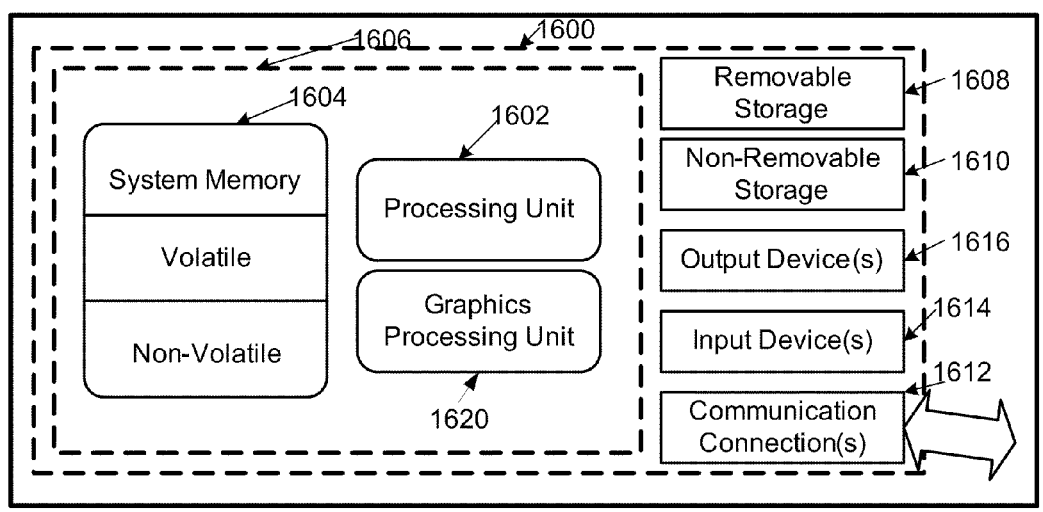
FIG. 16 is a flow diagram depicting an exemplary embodiment of a process for employing the virtual vision correction technique described herein wherein auto-tune logic is used to adapt a display to a user's vision correction needs by scaling font size.

FIG. 16 illustrates an example of a suitable computing system environment. The computing system environment is only one example of a suitable computing environment and is not intended to suggest any limitation as to the scope of use or functionality of the present technique. Neither should the computing environment be interpreted as having any dependency or requirement relating to any one or combination of components illustrated in the exemplary operating environment. With reference to FIG. 16, an exemplary system for implementing the virtual vision correction technique includes a computing device, such as computing device 1600. In its most basic configuration, computing device 1600 typically includes at least one processing unit 1602 and memory 1604. Depending on the exact configuration and type of computing device, memory 1604 may be volatile (such as RAM), non-volatile (such as ROM, flash memory, etc.) or some combination of the two. This most basic configuration is illustrated in FIG. 16 by dashed line 1606. Additionally, device 1600 may also have additional features/functionality. For example, device 1600 may also include additional storage (removable and/or non-removable) including, but not limited to, magnetic or optical disks or tape. Such additional storage is illustrated in FIG. 16 by removable storage 1608 and non-removable storage 1160. Computer storage media includes volatile and nonvolatile, removable and non-removable media implemented in any method or technology for storage of information such as computer readable instructions, data structures, program modules or other data. Memory 1604, removable storage 1608 and non-removable storage 1160 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by device 1600. Any such computer storage media may be part of device 1600.

Device 1600 also can contain communications connection(s) 1612 that allow the device to communicate with other devices and networks. Communications connection(s) 1612 is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media such as acoustic, RF, infrared and other wireless media. The term computer readable media as used herein includes both storage media and communication media.

Device 1600 may have various input device(s) 1614 such as a display, keyboard, mouse, pen, camera, touch input device, and so on. Output device(s) 1616 devices such as a display, speakers, a printer, and so on may also be included. All of these devices are well known in the art and need not be discussed at length here.

The virtual vision correction technique may be described in the general context of computer-executable instructions, such as program modules, being executed by a computing device. Generally, program modules include routines, programs, objects, components, data structures, and so on, that perform particular tasks or implement particular abstract data types. The virtual vision correction technique may be practiced in distributed computing environments where tasks are performed by remote processing devices that are linked through a communications network. In a distributed computing environment, program modules may be located in both local and remote computer storage media including memory storage devices.

It should also be noted that any or all of the aforementioned alternate embodiments described herein may be used in any combination desired to form additional hybrid embodiments. Although the subject matter has been described in language specific to structural features and/or methodological acts, it is to be understood that the subject matter defined in the appended claims is not necessarily limited to the specific features or acts described above. The specific features and acts described above are disclosed as example forms of implementing the claims.

What is claimed is:

1. A system for automatically adjusting a display, comprising:
    a computing device;
    a computer display;
    a computer program comprising program modules executable by the computing device, wherein the computing device is directed by the program modules of the computer program to,
    automatically, without vision testing, detect a user's increasing vision dissatisfaction with the computer display over time while using the computer display, based on the user's input device action error frequency compared to a previous period of time the user used the computing display; and
    if a user's input device action error frequency reaches a threshold accommodate changes in the user's vision over time, comprising repeatedly for a digital image displayed on the display:
        (a) applying a transformation to the digital image,
        (b) displaying the transformed image on the display,
        (c) prompting the user as to whether the user can clearly see the transformed image on the display;
        (d) receiving a response to the prompt from the user;
        (e) if the user responds to the prompt that the user cannot clearly see the transformed image repeating (a)-(d) until receiving an indication in response to the prompt from the user that the user can clearly see the transformed image on the display.

2. The system of claim 1, further comprising:
    wherein the indication in response to the prompt is spoken.

3. The system of claim 1,
    wherein the transformation increases font size of font displayed in the transformed image.

4. The system of claim 1, wherein the user's vision dissatisfaction with the display is further based on the number of key presses above a threshold determined in a previous time period of the user using the display.

5. The system of claim 1, wherein the computer display comprises a display on a wall.

6. The system of claim 1, wherein the transformation changes the color palette when applying the transformation to the digital image.

7. The system of claim 1, wherein the transformation changes the size of the digital image when applying the transformation to the digital image.

8. The system of claim 1, wherein the device input error frequency is measured by measuring typographical errors.

9. The system of claim 1, wherein the transformation highlights edges when applying the transformation to the digital image.

10. A computer-implemented process for adapting video displayed in video display glasses to a user's vision, comprising:
    using a computing device for:
        automatically, without vision testing or user feedback, detecting a user's increasing visual dissatisfaction while using the video display glasses compared to a previous period of time by monitoring the number of user's input device action errors;
        when the number of user's input device action errors reaches a threshold, changing the video displayed in the video display glasses, repeatedly over time, comprising:
            (a) changing video displayed on the video display glasses,
            (b) prompting the user as to whether the user can clearly see the changed video on the video display glasses;
            (c) receiving a response to the prompt from the user;
            (d) if the user responds to the prompt that the user cannot clearly see the changed video, repeat (a)-(c) until receiving an indication in response to the prompt from the user that the user can clearly see the changed video on the video display glasses.

11. The computer-implemented process of claim 10, further comprising automatically tuning the font size on the video displayed.

12. The computer-implemented process of claim 10, wherein changing the video displayed further comprises computing a transform to change the focus of the video on the display.

13. The computer-implemented process of claim 10, wherein changing the video displayed further comprises computing a transform to highlight edges in the video displayed on the display.

14. The computer-implemented process of claim 10, wherein changing the video displayed further comprises computing a transform to change the color palette of the video displayed on the display.

15. A computer-implemented process for adapting video displayed to a user's vision, comprising:
    using a computing device for:
        automatically, without vision testing, detecting a user's increasing visual dissatisfaction with a computer display over time by monitoring the user's input device action error frequency over time; and
        automatically adjusting an image, repeatedly over time, on the display to accommodate a user's changes in vision over time when the user's input key stroke frequency in a current period of time is over a threshold determined in a previous period of time, by iteratively:
        displaying a transformed image,
        prompting the user to indicate satisfaction with the displayed image,
        waiting for a response to the prompt,
        if the user responds to the prompt that the user is not satisfied with the displayed image, further transforming the displayed image
        until receiving an indication from the user that the user is satisfied with the displayed image in response to a prompt.

16. The computer-implemented process of claim 15, wherein the indication from the user is input with a microphone.

17. The computer-implemented process of claim 15, wherein the displayed transformed image increases displayed font size.

18. The computer-implemented process of claim 15, further comprising utilizing a graphics processor to aid in adjusting the image on the display.

19. The computer-implemented process of claim 18, further comprising utilizing special lenses to aid in adjusting the image on the display.

20. The computer-implemented process of claim 15, further comprising determining a user's vision characteristics prior to adjusting the image on the display by the user explicitly entering their vision prescription needs.

* * * * *